United States Patent [19]
Okada et al.

[11] Patent Number: 5,985,303
[45] Date of Patent: Nov. 16, 1999

[54] SHELF-LIFE EXTENDER FOR FOOD USE

[76] Inventors: Toru Okada, 688-3, Minori, Kakogawacho, Kakogawa, Hyogo, 675; Kenji Kuranari, 6-16-25, Chayama, Jounanku, Fukuoka, Fukuoka, 814-01, both of Japan

[21] Appl. No.: 08/691,561

[22] Filed: Aug. 2, 1996

[30] Foreign Application Priority Data

Aug. 11, 1995 [JP] Japan ................................. 7-227129
Aug. 23, 1995 [JP] Japan ................................. 7-239241

[51] Int. Cl.⁶ ............................................. A01N 25/10
[52] U.S. Cl. ..................... 424/405; 424/404; 424/406; 424/407; 424/410; 424/415; 424/485; 424/488; 426/270; 426/302; 426/326; 514/638; 514/514; 523/122
[58] Field of Search ................................. 424/404–407, 424/409, 410, 415, 485, 488; 523/122; 726/270, 326, 302, 309, 310; 514/638, 514

[56] References Cited

U.S. PATENT DOCUMENTS

| | | | |
|---|---|---|---|
| 3,996,386 | 12/1976 | Malikki et al. | 426/321 |
| 5,490,978 | 2/1996 | Spactro et al. | 424/49 |
| 5,512,213 | 4/1996 | Paterson | 252/400.62 |
| 5,632,972 | 5/1997 | Williams et al. | 424/49 |
| 5,635,796 | 6/1997 | Murphy | 424/409 |

FOREIGN PATENT DOCUMENTS

| | | |
|---|---|---|
| 4-207179A | 7/1992 | Japan . |
| 5-58805A | 3/1993 | Japan . |
| 6-192018A | 7/1994 | Japan . |
| 6-286775A | 10/1994 | Japan . |
| 7-46973A | 2/1995 | Japan . |

OTHER PUBLICATIONS

Blacon ed. Martindale—The Extra Pharmacopocia Garlic–p. 710 1974.

*Primary Examiner*—Neil S. Levy
*Attorney, Agent, or Firm*—Birch, Stewart, Kolasch & Birch, LLP

[57] ABSTRACT

The invention provides a shelf-life extender for upholding the freshness of food, such as meat, vegetables, fruits, etc., in retail packages or in a refrigerator for an extended period of time. An isothiocyanic acid compound is supported on a matrix such as a natural mucilaginous polysaccharide or a solid organic acid and the supported compound is packaged in synthetic resin film or nonwoven fabric. The invention further provides an aqueous gel composition comprising a specified surfactant, an isothiocyanic acid compound, and a gelling agent and a hydrophobic gel composition comprising a specified hydrophobic dispersion medium, an isothiocyanic acid compound, and a gelling agent.

8 Claims, No Drawings

SHELF-LIFE EXTENDER FOR FOOD USE

FIELD OF THE INVENTION

The present invention relates to a shelf-life extender (freshness-upholding agent) for food use which is capable of upholding the freshness of meat, fish, vegetables, and other foodstuffs.

Allyl isothiocyanate ($CH_2=CHCH_2NCS$) which occurs in horseradish and mustard inhibits growth of pathological microorganisms, particularly *Escherichia coli, Staphylococus aureus, Proteus* spp., and intestinal vibrio which are causative of food poisoning, and is of value as an agent for upholding the freshness of fish meat and animal meat. Furthermore, allyl isothiocyanate inhibits evolution of ethylene which is known as the aging hormone of vegetables and fruits and is, therefore, of great value as an agent for upholding the freshness of such foodstuffs. Meanwhile, horseradish and mustard extracts containing allyl isothiocyanate as a principle have been approved as food additives and can be safely disposed alongside food in a refrigerator. In addition, because allyl isothiocyanate acts as a shelf-life extender by gas-phase contact, its effect is felt even at low concentration (about 0.3 ppm).

Box lunches and other delicatessen items as well as vegetables, meat and fish are usually sold over the retail counter or put on distribution routes as prepackaged using a polystyrene foam or other plastic tray and a polyethylene or polypropylene film protective overwrap. When a shelf-life extender containing allyl isothiocyanate is enclosed in such a package, the emanated allyl isothiocyanate gas is easily dissipated from within the package so that the expected shelf-life extending effect is lost in a matter of hours. Regarding vegetables in particular, a shelf-life of at least about one week is required even on the retail shelf. Therefore, the concentration of allyl isothiocyanate within the package must be maintained at levels between 0.1 and 5 ppm for at least said period of time.

OBJECT AND SUMMARY OF THE INVENTION

Allyl isothiocyanate is a liquid compound which is hardly soluble in water and highly volatile, with a melting point of −100° C. and a boiling point of 151.9° C. Attempts have been made to uphold the freshness of food by impregnating a matrix such as a sheet of paper or a mineral substance with the compound and placing the supported compound in the food package or container. In such conventional arrangements, however, allyl isothiocyanate is quickly released from the matrix so that the shelf-life extending effect of the device is lost usually in 1–2 days. In order that the freshness of food may be maintained, it is necessary that a constant rate of emanation and an effective concentration (2–3 ppm) be maintained over an extended period of time.

The present invention has for its object to provide a shelf-life extender which upholds the freshness of food, such as meat, vegetables and fruits, as prepackaged or stored in a refrigerator, or food storage box over a long period of time. The present invention is characterized in the deposition of a horseradish extract, a mustard extract or an isothiocyanic acid compound such as allyl isothiocyanate on a matrix substance such as a natural polysaccharide or a solid organic acid and the formation of an aqueous or hydrophobic gel composition containing the same.

In its first aspect, the present invention provides a shelf-life extender for food use which comprises an isothiocyanic acid compound and a specified matrix substance supporting said compound and a prepackaged shelf-life extender using the same. The matrix substance is at least one member selected from the group consisting of naturally-occurring mucilaginous polysaccharides and organic acids which are solid at atmospheric temperature.

In a second aspect, the present invention provides an aqueous gel composition. The aqueous gel composition of the present invention comprises at least one surfactant selected from the group consisting of nonionic surfactants and amphoteric surfactants, an isothiocyanic acid compound, and a gelling agent. Thus, this composition contains a specified kind of surfactant.

In the conventional technology wherein allyl isothiocyanate is dispersed in a solvent such as a polyol, the active compound is dissipated in a short period of time. According to the research done by the inventors of the present invention, the preferred dispersing medium is a substance which is less volatile, compatible with an olephilic substance such as allyl isocyanate, and soluble in water as well. It is supposed that, in the present invention, the allyl isothiocyanate molecule is enclosed in the micelle formed by mutual attraction of non-volatile surfactant molecules, with the result that evaporation of allyl isothiocyanate is inhibited. In this aqueous gel, water accounts for at least about 80% and the mode of dispersion is of the oil-in-water type.

In a third aspect, the present invention provides a hydrophobic gel composition. This hydrophobic gel composition comprises at least one dispersion medium selected from the group consisting of isoparaffin, liquid paraffin, polyhydric alcohols, castor oil, and coconut oil, an isothiocyanic acid compound, and a gelling agent.

There has not been available a shelf-life extender that might be compared to the shelf-life extender composition of the present invention which is adapted to maintain the concentration of a horseradish extract or a mustard extract, or an isothiocyanic acid compound such as allyl isothiocyanate which is a principle of said extracts, at a constant concentration level within the package, refrigerator or food storage box to thereby uphold the freshness of food, such as meat, vegetables, or fruits, over a long period of time.

DETAILED DESCRIPTION OF THE INVENTION

The isothiocyanic acid compound that can be used as the active ingredient of the shelf-life extender for food use according to the present invention includes allyl isothiocyanate, butyl isothiocyanate, and their derivatives. Allyl isothiocyanate is particularly preferred. These isothiocyanic acid compounds can be native compounds or synthetic compounds. Furthermore, a horseradish or mustard extract which contains such compounds as active ingredients can likewise be employed.

(I) Shelf-life extender using a polysaccharide and/or a solid organic acid

In the shelf-life extender according to the first aspect of the present invention, the matrix for supporting the isothiocyanic acid compound includes naturally-occurring mucilaginous polysaccharides and organic acids which are solid at atmospheric temperature. Particularly preferred matrix substances are mentioned below. Incidentally, no stable shelf-life extender can be obtained using mineral matrices such as zeolite.

The natural mucilaginous polysaccharide (natural sizing agent) includes duran gum, guar gum, locust bean gum, xanthane gum, tara gum, carrageenan, agar, furcellaran, tamarind gum, curdlan, methoxypectin, pullulan, gum arabic, alginic acid and its salt, carboxymethylcellulose, soluble starch, etc. Preferred are xanthane gum, tamarind seed polysaccharide, guar gum, etc.

The organic acid that may be used includes hydroxydibasic acids such as tartaric acid, malic acid, citric acid, etc., dibasic acids such as adipic acid, malonic acid, succinic acid, etc., and sorbic acid, among others. Particularly preferred are adipic acid, sorbic acid, and malic acid.

These matrix substances can be used singly or in admixture. The morphology of the matrix substance may be pellet-like, powdery, granular, or in any form molded together with an auxiliary molding agent.

The amount of deposition of said isothiocyanic acid compound on the matrix is 0.001–30 weight % and preferably 0.2–8 weight % based on the weight of the matrix. If the proportion of the isothiocyanic acid compound is smaller than 0.001 weight %, the freshness-upholding effect of the composition will not be sufficient. On the other hand, deposition of the isothiocyanic acid compound in any amount larger than the above range will be technically difficult.

In the shelf-life extender of the present invention, a highly water-absorbent polymer can be used in combination with the matrix substance. Particularly when the shelf-life extender is used for a water-rich food, the biostatic effect of the isothiocyanic acid compound can be enhanced by including the highly water-absorbent polymer. Thus, since the isothiocyanic acid compound such as allyl isothiocyanate is olephilic, contact of the active substance with the water-rich food is difficult so that the biostatic effect is compromised. However, this disadvantage is ameliorated when the highly water-absorbent polymer is concomitantly employed.

The highly water-absorbent polymer for use in the present invention is a polymer which absorbs tens to thousands of times its own weight of water. As examples of such polymer, there can be mentioned crosslinked starch-acrylic acid salt graft copolymer (e.g. Sun Fresh ST-100, manufactured by Sanyo Chemical Industries, Ltd.), vinyl acetate-alkyl (meth) acrylate copolymer hydrolyzate metal salt, crosslinked vinyl alcohol-maleic acid copolymer, crosslinked vinyl alcohol-acrylic acid-maleic anhydride copolymer, crosslinked isobutylene-maleic acid copolymer, polyacrylonitrile graft polymer hydrolysate, starch-acrylic acid graft polymer, and so on.

A variety of techniques can be used for the production of the shelf-life extender using said matrix and isothiocyanic acid compound. A typical process comprises charging a pressure-resistant vessel with the matrix, evacuating the interior of the vessel to a reduced pressure of at least 20 mmHg, increasing the internal temperature of the vessel to 50–70° C., preferably 50–60° C., introducing the isothiocyanic acid compound such as allyl isothiocyanate into the vessel by, for example, spraying, and after sufficient gasification of the isothiocyanic acid compound in the vessel, bringing the internal pressure of the vessel back to atmospheric pressure to let the isothiocyanic acid compound adsorbed on the matrix.

When said highly water-absorbent polymer is used concomitantly, the isothiocyanic acid compound may be deposited on a premix of said matrix substance and highly water-absorbent polymer or the matrix substance carrying the isothiocyanic acid compound be mixed with the highly water-absorbent polymer.

The matrix entraps the isothiocyanic acid compound by adsorption or attraction and releases it gradually in very small amounts over a long period of time to uphold the freshness of food.

The resulting isothiocyanic acid compound-matrix may be packaged in a synthetic resin film such as vinylon (PVA) film, polyethylene film, nylon film, polybutadiene film, polypropylene film or the like and sealed by a known method such as heat sealing. A nonwoven fabric can also be used as the packaging material. Packaging is beneficial, for the vaporization of the isothiocyanic acid compound can be further controlled.

Particularly preferred are vinylon film, nylon film, polybutadiene film, laminates of such films with nonwoven cloth or porous polyethylene film and laminate films of cellophane with either nonwoven cloth or porous polyethylene film, all of which are moisture-permeable. When a solid organic acid having a small water-absorbent capacity is used as the matrix, the matrix may be packaged together with the highly water-absorbent polymer in a highly moisture-permeable laminate film and the resulting package be placed alongside a vegetable or the like in a product package. Then, the humidity within the product package is properly controlled to contribute much to the biostatic effect.

In this connection, if a laminate of cellophane film, vinylon (PVA) film, nylon film or the like, which is moisture-permeable but hardly heat-sealable, with a porous polyethylene film or a polyethylene-coated nonwoven cloth is used to package the isothiocyanic acid compound-matrix and the resulting package is used for the preservation of a food of high water content, much water enters into the isothiocyanic acid compound-matrix package, resulting in delamination of the film due to increased internal pressure. This trouble is obviated when a highly water-absorbent polymer is included in the package.

(II) Hydrophilic gel composition

The active ingredient of the hydrophilic gel composition according to the second aspect of the present invention is the same isothiocyanic acid compound as used in the first invention.

The proportion of said isothiocyanic acid compound in a hydrophilic gel composition is 0.1–10 weight % and preferably 0.2–3 weight %. If the proportion is smaller than the above range, no sufficient freshness-upholding effect will be obtained. On the other hand, if the above-mentioned range is exceeded, the gel will not be stable enough but undergo separation of water.

As the surfactant which is well compatible with said isothiocyanic acid compound and dispersible in water, nonionic surfactants and amphoteric surfactants can be mentioned. Particularly preferred surfactants are mentioned below. Incidentally, no stable gels of good quality are obtained when cationic or anionic surfactants are employed.

NONIONIC SURFACTANTS (A) Polyoxyethylene alkylphenyl ethers

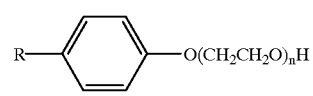

The preferred carbon number of R is 8, 9 or 12; the preferred HLB number is 8–16.

(B) Polyoxyethylene sorbitan fatty acid esters

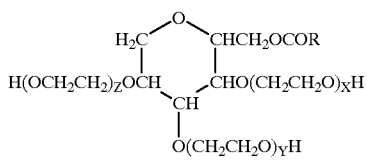

R (ester) is preferably lauryl, oleyl or stearyl; the preferred HLB number is 10–18.

(C) Polyoxyethylene fatty acid esters

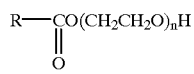

The preferred fatty acid is oleic acid, stearic acid or lauric acid; the preferred HLB number is 8–18.

(D) Polyoxyethylene alkyl ethers

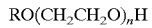

The preferred alkyl R is lauryl, cetyl or stearyl; the preferred HLB number is 8–18.

(E) Sorbitan fatty acid esters

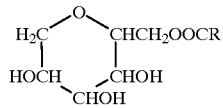

The preferred HLB number is not less than 6.

(F) Glycerin fatty acid esters

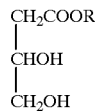

The preferred fatty acid for R is stearic acid or oleic acid.

(G) 1—1 coco-fatty acid diethanolamides

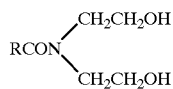

The above surfactants (A)–(G) belong to the following types, respectively.

A Polyoxyethylene phenyl ether type
B Polyoxyethylene sorbitan ester type
C Polyoxyethylene ester type
D Polyoxyethylene ether type
E Sorbitan ester type
F Polyol ester type
G Acid amide type

AMPHOTERIC SURFACTANTS

Cocoamide propyl betaine,

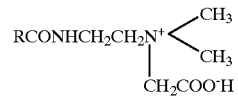

and carboxymethyl-N-hydroxyethyl-imidazolium betaine can be mentioned by way of example. These surfactants can be used singly or in combination.

The proportion of such surfactant is 0.1–30 g and preferably 1–5 g. If the proportion is smaller than the above range, no evaporation inhibitory effect will be obtained. On the other hand, if the surfactant is used in a larger proportion than the above range, no stable gel will be formed, with separation of water being inevitable.

The gelling agent for use in the aqueous gel composition of the present invention is a naturally-occurring mucilaginous polysaccharide (natural size) such as duran gum, guar gum, locust bean gum, xanthane gum, tara gum, carrageenan, agar, furcellaran, tamarind gum, curdlan, methoxypectin, pullulan, gum arabic, alginic acid and its salt, carboxymethylcellulose, soluble starch, etc. Particularly preferred are duran gum and carrageenan.

The proportion of such gelling agent based on the total weight of the gel is 0.1–5 weight %, preferably 1–10 weight %, and for still better results, 1–3 weight %. If the proportion of the gelling agent is smaller, no stable gel will be formed. If the proportion is larger than the above range, the viscosity buildup during the production of a gel results in poor gel quality.

Known gelation technology aqueous can be used for the production of the aqueous gel composition of the present invention. A typical process comprises heating and dissolving the gelling agent in water, mixing the surfactant and isothiocyanic acid compound with the solution, and cooling the mixture for gelation to provide an aqueous gel composition adapted to release the isothiocyanic acid compound at a controlled rate. Typically 1 g of Kelco Gel (duran gum, Kelco Co.) is dissolved in 93 g of water. After this solution is heated to 90° C., 5 g of polyoxyethylene nonyl-phenyl ether (HLB, 15.2) is added and the mixture is stirred. After heating is stopped, 1 g of allyl isothiocyanate is added and the mixture is cooled for gelation. When the solution is cooled to about 60° C., gelation takes place rapidly.

In the resulting gel, the surfactant molecules form a micelle with their oleophilic groups arranged inside and the isothiocyanate entrapped within the micelle, with the result that the emanation of isothiocyanate gas is suppressed by mutual attraction. At the interface between the gel and the atmospheric air, the oleophilic groups are adjacent to the air while the hydrophilic groups are disposed inside the gel to form a film compatible with allyl isothiocyanate so that the emanation of the isothiocyanic acid compound gas is further inhibited to insure a more positive controlled-release effect.

(III) Hydrophobic gel composition

The hydrophobic gel composition according to the third aspect of the present invention also contains the same isothiocyanate compound as described above as an active ingredient. The proportion of the isothiocyanic acid compound in the gel is 0.1–30 weight % and preferably 1–10 weight %.

The hydrophobic dispersion medium with good compatibility with the isothiocyanic acid compound includes isoparaffin, liquid paraffin, polyols such as propylene glycol, castor oil, coconut oil, and so on. Among them, isoparaffin is preferred which permits a visual assessment of the residual useful life following the progressive decrease in gel volume.

The gelling agent that can be used in the hydrophobic gel composition of the present invention includes hydroxystearic acid compounds such as 1,1-hydroxystearic acid, 1,2-hydroxystearic acid, etc., and N-lauroyl-L-glutamyl-α,γ-di-n-butyramide, among others. Particularly preferred are hydroxystearic acid compounds. The proportion of the gelling agent is 0.1–15 weight % and preferably 1–10 weight % based on the total weight of the gel. If the proportion of the gelling agent is smaller, no stable gel will be obtained. On the other hand, if it is larger than the above range, the viscosity buildup during formation of a gel will result in a gel of poor quality.

Any suitable method can be used for the production of a hydrophobic gel composition of the present invention. A typical process comprises melting the gelling agent and dispersion medium under heating, then adding allyl isothiocyanate, for instance, and cooling the mixture.

By the above gelation technology, a hydrophobic gel composition adapted to release the isothiocyanic acid compound at a controlled rate can be obtained.

EXAMPLES

The following examples are further illustrative but by no means limitative of the present invention.

Example A-1

A bench-top autoclave was charged with 100 g of xanthane gum (Kelco, tradename Kelzan) and, after evacuation (10 mmHg), 1 g of allyl isothiocyanate was introduced so as to fill the plenum with allyl isothiocyanate gas. The internal pressure of the autoclave was returned to atmospheric pressure, whereupon the allyl isothiocyanate was liquefied and adsorbed on the matrix gum to provide a powdery shelf-life extender.

Then, 1 g of the shelf-life extender was packaged in two different manners, using polyvinyl alcohol film (20 μm, 3 cm×3 cm) and nonwoven cloth (30 μm, 3 cm×3 cm, polyester-rayon). Each of these prepackaged shelf-life extenders was placed alongside a loaf of fresh beef in a polyethylene tray covered with polyethylene film (20 μm) and allowed to stand (20° C.). Then, the gas within the covered polyethylene tray was serially sampled and analyzed by gas chromatography. The appearance of beef was also monitored.

[Gas chromatographic conditions]

| Column stationary phase | Thermon 3000 |
| Column temperature | 120° C. |
| Carrier gas | $N_2$ |
| Carrier gas pressure | 0.5 kg/cm$^2$ |

Examples A-(2–7) and Comparative Examples A-(1–2)

According to the recipes given in Table A-1 and Table A-2, prepackaged shelf-life extenders were prepared using allyl isothiocyanate and various matrix materials in otherwise the same manner as Example A-1. However, vinylon bags were used for Examples A-2 and A-3, nonwoven cloth bags for Examples A-4 and A-5, polypropylene bags for A-6, and polyethylene bags for Example A-7. The polyethylene and polypropylene bags were sized 3 cm×3 cm (film thickness 20 μm) and the vinylon and nonwoven cloth bags were the same as those used in Example A-1. Comparative Example A-1 represents a blank experiment in which no shelf-life extender was used, and Comparative Example A-2 is the conventional shelf-life extender using a cyclodextrin matrix.

Examples A-(8–13)

Adipic acid and a highly water-absorbent polymer (Sun Fresh ST-100, Sanyo Chemical Industries, Ltd.) were mixed according to the recipes given in Table A-1 and Table A-2 and the respective mixtures were treated as in Example A-1 for adsorption of allyl isothiocyanate. Each of the mixtures was packaged in cellophan-polyethylene laminate film to provide a prepackaged shelf-life extender.

TABLE A-1

| Component | Example A |  |  |  |  |  |  |  |  |  |
|---|---|---|---|---|---|---|---|---|---|---|
|  | 1 | 2 | 3 | 4 | 5 | 6 | 7 | 8 | 9 | 10 |
| Allyl isothiocyanate | 1 | 0.5 | 0.5 | 0.5 | 0.5 | 0.5 | 0.5 | 1 | 1 | 1 |
| Xanthane gum | 100 | 100 | 100 |  |  |  | 50 |  |  |  |
| Tamarind seed polysaccharide |  |  | 100 |  |  |  |  |  |  |  |
| Guar gum |  |  |  | 100 |  |  |  |  |  |  |
| Sorbic acid |  |  |  |  | 100 |  | 50 |  |  |  |
| Adipic acid |  |  |  |  |  | 100 |  | 70 | 80 | 90 |
| Highly water-absorbent polymer |  |  |  |  |  |  |  | 30 | 20 | 10 |
| Cyclodextrin |  |  |  |  |  |  |  |  |  |  |

| Packaging material | Vinylon |  | Nonwoven fabric |  | Vinylon | Vinylon | Nonwoven fabric | Nonwoven fabric | PP Ap- | PE Ap- | *1 |  | *2 |  | *3 |  |
|---|---|---|---|---|---|---|---|---|---|---|---|---|---|---|---|---|
| Change in appearance | Appearance | Conc. | Appearance | Conc. | Appearance | Appearance | Appearance | Appearance | pearance | pearance | Appearance | Conc. | Appearance | Conc. | Appearance | Conc. |
| After 1 hr | – | 2 | – | 4 |  |  |  |  |  |  | – | 6 | – | 5 | – | 6 |
| After 3 hr | – | 3 | – | 5 |  |  |  |  |  |  | – | 5 | – | 5 | – | 5 |
| After 5 hr | – | 3 | – | 5 | – | – | – | – | – | – | – | 5 | – | 5 | – | 5 |
| After 10 hr | – | 3 | – | 5 |  |  |  |  |  |  | – | 5 | – | 5 | – | 5 |
| After 15 hr | – | 4 | – | 5 |  |  |  |  |  |  | – | 4 | – | 5 | – | 4 |
| After 20 hr |  |  |  |  | – | – | – | – | – | – | – | 4 | – | 4 | – | 4 |

TABLE A-1-continued

| | | | | | | | |
|---|---|---|---|---|---|---|---|
| After 24 hr | − | 3 | − | 5 | − 4 | − 4 | − 4 |
| Viable count after 24 hr | | | | | $2 \times 10^4$ | $3.5 \times 10^4$ | $2.5 \times 10^4$ |

Note)
Appearance: − no color change; ± slight color change; + definite color change
Concentration unit: ppm
*1: cellophan/polyethylene laminate
*2: nylon/nonwoven fabric laminate
*3: vinylon/nonwoven fabric laminate
Conc. = concentration

TABLE A-2

| | Example A | | | Comparative Example A | |
|---|---|---|---|---|---|
| Component | 11 | 12 | 13 | 1 | 2 |
| Allyl isothiocyanate | 1 | 1 | 1 | | 1 |
| Xanthane gum | | | | | |
| Tamarind seed polysaccharide | | | | | |
| Guar gum | | | | | |
| Sorbic acid | | | | | |
| Adipic acid | 85 | 85 | 85 | | |
| Highly water-absorbent polymer | 15 | 15 | 15 | | |
| Cyclodextrin | | | | | 100 |
| Packaging material | *4 | Vinylon/PE | Vinylon/PE | | PE |

| Change in appearance | Appearance | Conc. | Appearance | Conc. | Appearance | Conc. | Appearance | Conc. | Appearance | Conc. |
|---|---|---|---|---|---|---|---|---|---|---|
| After 1 hr | − | 5 | − | 3 | − | 5 | − | 0 | − | 2 |
| After 3 hr | − | 6 | − | 5 | − | 4 | − | 0 | − | 10 |
| After 5 hr | − | 5 | − | 6 | − | 6 | ± | 0 | − | 15 |
| After 10 hr | − | 5 | − | 5 | − | 5 | ± | 0 | − | 1 |
| After 15 hr | − | 5 | − | 4 | − | 4 | ± | 0 | ± | 0 |
| After 20 hr | − | 4 | − | 4 | − | 4 | + | 0 | + | 0 |
| After 24 hr | − | 4 | − | 4 | − | 4 | + | 0 | + | 0 |
| Viable count after 24 hr | | | | | | | $3 \times 10^8$ | | | |

Note)
Appearance: − no color change; ± slight color change; + definite color change
Concentration unit: ppm
*4: cellophan/nonwoven fabric laminate
Conc. = concentration It will be apparent from Tables A-1 and A-2 that discoloration took place within 5 hours in Comparative Example A-1 (blank) and that the concentration of allyl isothiocyanate was not well sustained in Comparative Example A-2.

Examples B-(1–15) and Comparative Examples B-(1–3)

Using allyl isothiocyanate, surfactant, and gelling agent according to the recipes shown in Table B-1, gel compositions (with water added to make 100 g) were prepared in the same manner as the production of aqueous gel compositions described above. Each gel composition was allowed to stand in open condition at 20° C. and 65% RH for 1, 5, 10, 15 and 20 days. The samples thus obtained were respectively stored in a refrigerator (200 L) for 1 hour and the gas within the refrigerator was sampled and analyzed by gas chromatography as described above.

TABLE B-1

| | | Example B | | | | | | | | | | | | | | | Comparative Example B | | |
|---|---|---|---|---|---|---|---|---|---|---|---|---|---|---|---|---|---|---|---|
| Component | | 1 | 2 | 3 | 4 | 5 | 6 | 7 | 8 | 9 | 10 | 11 | 12 | 13 | 14 | 15 | 1 | 2 | 3 |
| Allyl isothiocyanate | | 1 | 1 | 1 | 1 | 1 | 1 | 1 | 1 | 1 | 1 | 1 | 1 | 3 | 3 | 1 | 1 | 1 | |
| Surfac- | Polyoxyethylene nonylphenyl ether | 5 | 3 | 5 | | | 3 | 3 | 3 | | 3 | 3 | | | | | | | |

TABLE B-1-continued

| | | Example B | | | | | | | | | | | | | | | Comparative Example B | | |
|---|---|---|---|---|---|---|---|---|---|---|---|---|---|---|---|---|---|---|---|
| Component | | 1 | 2 | 3 | 4 | 5 | 6 | 7 | 8 | 9 | 10 | 11 | 12 | 13 | 14 | 15 | 1 | 2 | 3 |
| tant Polyoxyethylene monostearate | | | | 3 | | | | | | 2 | 3 | | 1 | | | | | | |
| Polyoxyethylene sorbitan monostearate | | | | | 3 | 3 | | | | | | 3 | | 1 | | | | | |
| Glycerin monostearate | | | | | | | 3 | 3 | | | | | 3 | | | | | | |
| Sorbitan monostearate | | | | | | | | 1 | 1 | | | | | | | | | | |
| Coco-fatty acid diethanolamide | | | | | | | | | | | | | | | 3 | | | | |
| Coco-amide propyl betaine | | 3 | | | | | | 2 | | 2 | | | | | | | | | |
| Polyoxyethylene laurylsulfate Na | | | | | | | | | | | | | | | | | | 3 | |
| Benzalkonium chloride | | | | | | | | | | | | | | | | | | | 3 |
| Duran gum (Kelco Gel) | | | 1 | 1 | 1 | 1 | 1 | 1 | 1 | 1 | 1 | 1 | 1 | 1 | | | 1 | 1 | 1 |
| Isoparaffin compound (b.p. 100–250° C.) | | | | | | | | | | | | | | | 88 | 94 | | | |
| 1,1-Hydroxystearic acid | | | | | | | | | | | | | | | 9 | | | | |
| N-Lauroyl-L-glutamyl-α,γ-di-n-butyramide | | | | | | | | | | | | | | | | 3 | | | |
| Concentration (ppm) After 1 day | | 20 | 23 | 20 | 22 | 20 | 19 | 20 | 19 | 18 | 20 | 18 | 20 | 20 | 20 | 20 | 20 | 10 | 10 |
| within refrigerator After 5 days | | 18 | 15 | 15 | 15 | 15 | 15 | 14 | 15 | 17 | 16 | 15 | 14 | 15 | 15 | 16 | 4 | 1 | 1 |
| After 10 days | | 10 | 9 | 8 | 8 | 9 | 9 | 10 | 8 | 10 | 10 | 9 | 9 | 10 | 14 | 13 | 0 | 0 | 0 |
| After 15 days | | 5 | 4 | 4 | 4 | 3 | 3 | 5 | 4 | 6 | 5 | 4 | 4 | 6 | 10 | 9 | 0 | 0 | 0 |
| After 25 days | | 5 | 4 | 4 | 4 | 3 | 3 | 5 | 4 | 3 | 5 | 4 | 4 | 5 | 10 | 9 | 0 | 0 | 0 |

In the case of the gel composition according to Comparative Example B-1 (without a surfactant), the concentration of allyl isothiocyanate was not sufficiently sustained. In Comparative Example B-2 (an anionic surfactant)r allyl isothiocyanate reacted with the surfactant, failing to give a satisfactory gel. In Comparative Example B-3 (a cationic surfactant), the gel was of low strength and unstable, showing separation of water.

The shelf-life extender of the present invention serves to uphold the freshness of meat, vegetables and fruits for a long time in the package, refrigerator or food storage box.

What is claimed is:

1. A shelf life extender for food which comprises 0.001 to 30 wt % of an isothiocyanic acid compound supported through a matrix selected from the group consisting of a natural mucilaginous polysaccharide and a solid organic acid.

2. The shelf-life extender for food as claimed in claim 1 which contains a solid organic acid as said matrix together with a water-absorbent polymer.

3. The shelf-life extender for food as claimed in claim 1, wherein said matrix is xanthane gum, tamarind seed polysaccharide, guar gum, sorbic acid, adipic acid or malic acid.

4. The shelf-life extender for food as claimed in claim 1, wherein said isothiocyanic acid compound is allyl isothiocyanate.

5. A process for producing the shelf-life extender of claim 1 which comprises subjecting at least one matrix substance selected from the group consisting of natural mucilaginous polysaccharides and solid organic acids to elevated temperature and reduced pressure;
  feeding an isothiocyanic acid compound thereto; and
  returning the pressure to atmospheric pressure to let said isothiocyanic acid compound be supported by said matrix substance.

6. A packaged shelf-life extender for food which comprises the shelf-life extender of claim 1 as packaged in synthetic resin film, cellophane or nonwoven cloth.

7. A shelf-life extender for food which is a hydrophobic gel composition comprising at least one dispersion medium selected from the group consisting of isoparaffin, liquid paraffin, and polyhydric alcohols; an isothiocyanic acid compound; and at least one gelling agent selected from the group consisting of 1,1-hydroxystearic acid, 1,2-hydroxystearic acid, and N-lauroyl-L-glutamyl-δ,γ-di-n-butyramide.

8. A method of maintaining the freshness of a food which comprises placing with said food, a shelf-life extender for food which comprises 0.001 to 30 wt. % of an isothiocyanic acid compound supported through a matrix selected from the group consisting of a natural mucilaginous polysaccharide and a solid organic acid.

* * * * *